(12) United States Patent
Ashish et al.

(10) Patent No.: US 10,167,475 B2
(45) Date of Patent: Jan. 1, 2019

(54) APTAMERS FOR PURIFYING AND QUANTIFYING GELSOLIN AND ITS VARIANTS

(71) Applicant: Council of Scientific & Industrial Research, New Delhi (IN)

(72) Inventors: Ashish, Chandigarh (IN); Renu Garg, Chandigarh (IN); Nagesh Peddada, Chandigarh (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 15/509,800

(22) PCT Filed: Oct. 5, 2015

(86) PCT No.: PCT/IN2015/050128
§ 371 (c)(1),
(2) Date: Mar. 8, 2017

(87) PCT Pub. No.: WO2016/056028
PCT Pub. Date: Apr. 14, 2016

(65) Prior Publication Data
US 2017/0260530 A1 Sep. 14, 2017

(30) Foreign Application Priority Data
Oct. 7, 2014 (IN) .......................... 2852/DEL/2014

(51) Int. Cl.
| | | |
|---|---|---|
| *C07H 21/04* | (2006.01) | |
| *C12N 15/115* | (2010.01) | |
| *C07K 14/47* | (2006.01) | |
| *G01N 33/68* | (2006.01) | |
| *C07K 1/22* | (2006.01) | |
| *G01N 33/53* | (2006.01) | |

(52) U.S. Cl.
CPC .............. *C12N 15/115* (2013.01); *C07K 1/22* (2013.01); *C07K 14/4702* (2013.01); *G01N 33/5308* (2013.01); *G01N 33/68* (2013.01); *G01N 33/6872* (2013.01); *C12N 2310/16* (2013.01); *C12N 2320/10* (2013.01); *G01N 2333/4703* (2013.01); *G01N 2333/4727* (2013.01)

(58) Field of Classification Search
None
See application file for complete search history.

(56) References Cited

U.S. PATENT DOCUMENTS 9,895,414 B2 * 2/2018 Cowin ............... A61K 38/1709

OTHER PUBLICATIONS

Arndt-Jovin DJ, Jovin TM, Bahr W, Frischauf AM, Marquardt M, Covalent attachment of DNA to agarose. Improved synthesis and use in affinity chromatography. European journal of biochemistry / FEBS 54: 411-418 (1975). EU.

Ashish, Paine MS, Perryman PB, Yang L, Yin HL, Krueger JK, Global structure changes associated with Ca2+ activation of full-length human plasma gelsolin. J Biol Chem 282: 25884-25892 (2007) US.

Bucki R, Byfield FJ, Kulakowska A, McCormick ME, Drozdowski W, Namiot Z, Hartung T, Janmey PA, Extracellular gelsolin binds lipoteichoic acid and modulates cellular response to proinflammatory bacterial wall components. Journal of immunology 181: 4936-4944 (2008) US.

Bucki R, Georges PC, Espinassous Q, Funaki M, Pastore JJ, Chaby R, Janmey PA, Inactivation of endotoxin by human plasma gelsolin. Biochemistry 44: 9590-9597 (2005) US.

Bucki R, Kulakowska A, Byfield FJ, Zendzian-Piotrowska M, Baranowski M, Marzec M, Winer JP, Ciccarelli NJ, Gorski J, Drozdowski W, Bittman R, Janmey PA, Plasma gelsolin modulates cellular response to sphingosine 1-phosphate. American journal of physiology Cell physiology 299: C1516-1523 (2010) US.

Garg R, Peddada N, Sagar A, Nihalani D, Ashish, Visual insight into how low pH alone can induce actin-severing ability in gelsolin under calcium-free conditions. J Biol Chem 286: 20387-20397 (2011) US.

Ito H, Kambefi, Kimura Y, Nakamura H, Hayashi E, Kishimoto T, Kishimoto S, Yamamoto H, Depression of plasma gelsolin level during acute liver injury. Gastroenterology 102: 1686-1692 (1992) JP.

Kadonaga JT, Tjian R, Affinity purification of sequence-specific DNA binding proteins. Proceedings of the National Academy of Sciences of the United States of America 83: 5889-5893 (1986) US.

Kwiatkowski DJ, Mehl R, Izumo S, Nadal-Ginard B, Yin HL, Muscle is the major source of plasma gelsolin. The Journal of biological chemistry 263: 8239-8243 (1988) US.

Kwiatkowski DJ, Stossel TP, Orkin SH, Mole JE, Colten HR, Yin HL, Plasma and cytoplasmic gelsolins are encoded by a single gene and contain a duplicated actin-binding domain. Nature 323: 455-458 (1986) US.

Lee PS, Waxman AB, Cotich KL, Chung SW, Perrella MA, Stossel TP, Plasma gelsolin is a marker and therapeutic agent in animal sepsis. Crit Care Med 35: 849-855 (2007) US.

Lee WM, Galbraith RM, The extracellular actin-scavenger system and actin toxicity. N Engl J Med 326: 1335-1341 (1992) US.

Lind SE, Janmey PA, Human plasma gelsolin binds to fibronectin. J Biol Chem 259: 13262-13266 (1984) US.

Lind SE, Smith DB, Janmey PA, Stossel TP, Depression of gelsolin levels and detection of gelsolin-actin complexes in plasma of patients with acute lung injury. Am Rev Respir Dis 138: 429-434 (1988) US.

(Continued)

*Primary Examiner* — Kimberly Chong

(74) *Attorney, Agent, or Firm* — Belles Katz LLC

(57) ABSTRACT

The present invention relates to novel DNA aptamers capable of binding gelsolin tightly and specifically. The invention further relates to the use of these aptamers to estimate the gelsolin levels in a given sample and purify bulk quantities of tagless gelsolin and its variants. The present invention thus eliminates the use of different animals/their tissues to produce gelsolin binding proteins, which are much more expensive and socially unacceptable methods as opposed to the synthesis of a DNA molecule by in vitro PCR. Using this strategy, bulk production of the gelsolin binding matrix can be carried out at much lower cost. Also, the aptamers can be used to block binding of gelsolin to its binding partners for diagnostic and/or therapeutic applications.

4 Claims, 6 Drawing Sheets

Figure 1:
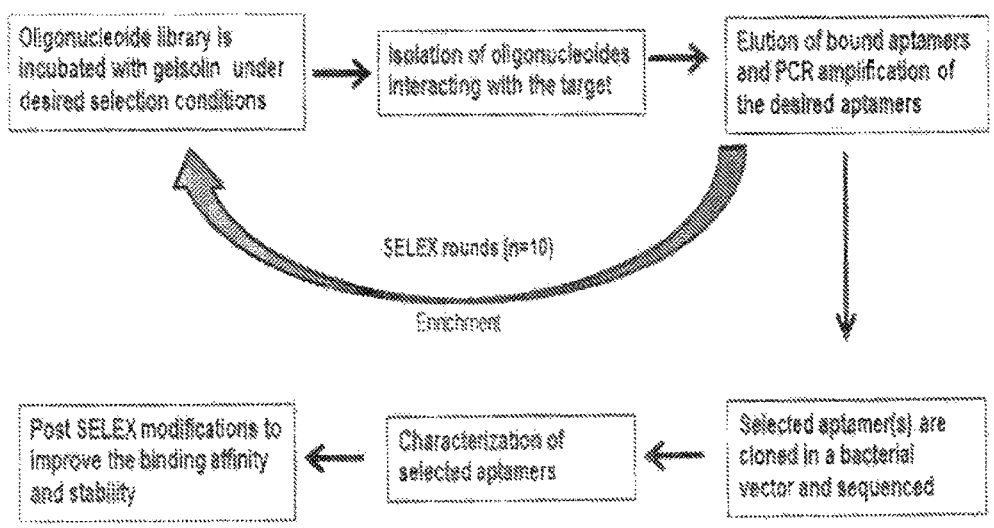

Specification includes a Sequence Listing.

(56) References Cited

OTHER PUBLICATIONS

Lofberg M, Paunio T, Tafitela R, Kiuru S, Somer H, Serum gelsolin and rhabdomyolysis. J Neurol Sci 157: 187-190 (1998) FI.

Osborn TM, Dahlgren C, Hartwig JH, Stossel TP, Modifications of cellular responses to lysophosphatidic acid and platelet-activating factor by plasma gelsolin. American journal of physiology Cell physiology 292: C1323-1330 (2007) US.

Osborn TM, Verdrengh M, Stossel TP, Tarkowski A, Bokarewa M, Decreased levels of the gelsolin plasma isoform in patients with rheumatoid arthritis. Arthritis research & therapy 10: R117 (2008) SE.

Pan W, Clawson GA, The shorter the better: reducing fixed primer regions of oligonucleotide libraries for aptamer selection. Molecules 14: 1353-1369 (2009) US.

Peddada N, Sagar A, Ashish, Garg R, Plasma gelsolin: a general prognostic marker of health. Med Hypotheses 78: 203-210 (2012) IN.

Peddada N, Sagar A, Rathore YS, Choudhary V, Pattnaik UB, Khatri N, Garg R, Ashish, Global shapes of F-actin depolymerization-competent minimal gelsolins: insight into the role of g2-g3 linker in pH/Ca2+ insensitivity of the first half. J Biol Chem 288: 28266-28282 (2013) IN.

Smith DB, Janmey PA, Sherwood JA, Howard RJ, Lind SE, Decreased plasma gelsolin levels in patients with Plasmodium falciparum malaria: a consequence of hemolysis? Blood 72: 214-218 (1988) US.

Suhler E, Lin W, Yin HL, Lee WM, Decreased plasma gelsolin concentrations in acute liver failure, myocardial infarction, septic shock, and myonecrosis. Crit Care Med 25: 594-598 (1997) US.

Sun HQ, Yamamoto M, Mejillano M, Yin HL, Gelsolin, a multi-functional actin regulatory protein. The Journal of biological chemistry 274: 33179-33182 (1999) US.

Vouyiouklis DA, Brophy PJ, A novel gelsolin isoform expressed by oligodendrocytes in the central nervous system. Journal of neurochemistry 69: 995-1005 (1997) SCT.

Wen D, Corina K, Chow EP, Miller S, Janmey PA, Pepinsky RB, The plasma and cytoplasmic forms of human gelsolin differ in disulfide structure. Biochemistry 35: 9700-9709 (1996) US.

Yin HL, Kwiatkowski DJ, Mole JE, Cole FS, Structure and biosynthesis of cytoplasmic and secreted variants of gelsolin. J Biol Chem 259: 5271-5276 (1984) US.

Yin HL, Stull JT, Proteins that regulate dynamic actin remodeling in response to membrane signaling minireview series. The Journal of biological chemistry 274: 32529-32530 (1999) US.

Yu FX, Zhou DM, Yin HL, Chimeric and truncated gCap39 elucidate the requirements for actin filament severing and and capping by the gelsolin family of proteins. J Biol Chem 266: 19269-19275 (1991) US.

Haverland, Nicole et al: "Immunoreactivity of anti-gelsolin antibodies: implications for biomarker validation", Journal of Translational Medicine, Biomed Central, London, GB, vol. 8, No. 1, Dec. 20, 2010, p. 137, XP021088855, ISSN: 1479-5876, DOI: 10.1186/1479-5876-8-137.

Stoltenburg et al: "SELEX—A (r)evolutionary method to generate high-affinity nucleic acid ligands", Biomolecular engineering, Elsevier, New York, NY, US, vol. 24, No. 4, Sep. 16, 2007, pp. 381-403, XP022251573, ISSN: 1389-0344, DOI: 10.1016/J.BIOENG.2007.06.001.

Corresponding International Preliminary Report on Patentability for PCT/IN2015/050128 dated Sep. 22, 2016.

Corresponding International Search Report and Written Opinion for PCT/IN2015/050128 dated Apr. 12, 2016.

* cited by examiner

SEQUENCE LISTING

```
<160> NUMBER OF SEQ ID NOS: 9

<210> SEQ ID NO 1
<211> LENGTH: 782
<212> TYPE: PRT
<213> ORGANISM: Homo sapiens
<220> FEATURE:
<221> NAME/KEY: Gelsolin Mature Protein
<222> LOCATION: (28)..(782)

<400> SEQUENCE: 1

Met Ala Pro His Arg Pro Ala Pro Ala Leu Leu Cys Ala Leu Ser Leu
1               5                   10                  15

Ala Leu Cys Ala Leu Ser Leu Pro Val Arg Ala Ala Thr Ala Ser Arg
            20                  25                  30
```

-continued

```
Gly Ala Ser Gln Ala Gly Ala Pro Gln Gly Arg Val Pro Glu Ala Arg
             35                  40                  45

Pro Asn Ser Met Val Val Glu His Pro Glu Phe Leu Lys Ala Gly Lys
 50                  55                  60

Glu Pro Gly Leu Gln Ile Trp Arg Val Glu Lys Phe Asp Leu Val Pro
 65                  70                  75                  80

Val Pro Thr Asn Leu Tyr Gly Asp Phe Phe Thr Gly Asp Ala Tyr Val
                 85                  90                  95

Ile Leu Lys Thr Val Gln Leu Arg Asn Gly Asn Leu Gln Tyr Asp Leu
            100                 105                 110

His Tyr Trp Leu Gly Asn Glu Cys Ser Gln Asp Glu Ser Gly Ala Ala
            115                 120                 125

Ala Ile Phe Thr Val Gln Leu Asp Asp Tyr Leu Asn Gly Arg Ala Val
        130                 135                 140

Gln His Arg Glu Val Gln Gly Phe Glu Ser Ala Thr Phe Leu Gly Tyr
145                 150                 155                 160

Phe Lys Ser Gly Leu Lys Tyr Lys Lys Gly Gly Val Ala Ser Gly Phe
                165                 170                 175

Lys His Val Val Pro Asn Glu Val Val Val Gln Arg Leu Phe Gln Val
            180                 185                 190

Lys Gly Arg Arg Val Val Arg Ala Thr Glu Val Pro Val Ser Trp Glu
        195                 200                 205

Ser Phe Asn Asn Gly Asp Cys Phe Ile Leu Asp Leu Gly Asn Asn Ile
            210                 215                 220

His Gln Trp Cys Gly Ser Asn Ser Asn Arg Tyr Glu Arg Leu Lys Ala
225                 230                 235                 240

Thr Gln Val Ser Lys Gly Ile Arg Asp Asn Glu Arg Ser Gly Arg Ala
                245                 250                 255

Arg Val His Val Ser Glu Glu Gly Thr Glu Pro Glu Ala Met Leu Gln
            260                 265                 270

Val Leu Gly Pro Lys Pro Ala Leu Pro Ala Gly Thr Glu Asp Thr Ala
        275                 280                 285

Lys Glu Asp Ala Ala Asn Arg Lys Leu Ala Lys Leu Tyr Lys Val Ser
290                 295                 300

Asn Gly Ala Gly Thr Met Ser Val Ser Leu Val Ala Asp Glu Asn Pro
305                 310                 315                 320

Phe Ala Gln Gly Ala Leu Lys Ser Glu Asp Cys Phe Ile Leu Asp His
                325                 330                 335

Gly Lys Asp Gly Lys Ile Phe Val Trp Lys Gly Lys Gln Ala Asn Thr
            340                 345                 350

Glu Glu Arg Lys Ala Ala Leu Lys Thr Ala Ser Asp Phe Ile Thr Lys
        355                 360                 365

Met Asp Tyr Pro Lys Gln Thr Gln Val Ser Val Leu Pro Glu Gly Gly
370                 375                 380

Glu Thr Pro Leu Phe Lys Gln Phe Phe Lys Asn Trp Arg Asp Pro Asp
385                 390                 395                 400

Gln Thr Asp Gly Leu Gly Leu Ser Tyr Leu Ser Ser His Ile Ala Asn
                405                 410                 415

Val Glu Arg Val Pro Phe Asp Ala Ala Thr Leu His Thr Ser Thr Ala
            420                 425                 430

Met Ala Ala Gln His Gly Met Asp Asp Asp Gly Thr Gly Gln Lys Gln
        435                 440                 445
```

```
Ile Trp Arg Ile Glu Gly Ser Asn Lys Val Pro Val Asp Pro Ala Thr
450                 455                 460

Tyr Gly Gln Phe Tyr Gly Gly Asp Ser Tyr Ile Ile Leu Tyr Asn Tyr
465                 470                 475                 480

Arg His Gly Gly Arg Gln Gly Gln Ile Ile Tyr Asn Trp Gln Gly Ala
                485                 490                 495

Gln Ser Thr Gln Asp Glu Val Ala Ala Ser Ala Ile Leu Thr Ala Gln
            500                 505                 510

Leu Asp Glu Glu Leu Gly Gly Thr Pro Val Gln Ser Arg Val Val Gln
            515                 520                 525

Gly Lys Glu Pro Ala His Leu Met Ser Leu Phe Gly Gly Lys Pro Met
530                 535                 540

Ile Ile Tyr Lys Gly Gly Thr Ser Arg Glu Gly Gln Thr Ala Pro
545                 550                 555                 560

Ala Ser Thr Arg Leu Phe Gln Val Arg Ala Asn Ser Ala Gly Ala Thr
                565                 570                 575

Arg Ala Val Glu Val Leu Pro Lys Ala Gly Ala Leu Asn Ser Asn Asp
            580                 585                 590

Ala Phe Val Leu Lys Thr Pro Ser Ala Ala Tyr Leu Trp Val Gly Thr
            595                 600                 605

Gly Ala Ser Glu Ala Glu Lys Thr Gly Ala Gln Glu Leu Leu Arg Val
610                 615                 620

Leu Arg Ala Gln Pro Val Gln Val Ala Glu Gly Ser Glu Pro Asp Gly
625                 630                 635                 640

Phe Trp Glu Ala Leu Gly Gly Lys Ala Ala Tyr Arg Thr Ser Pro Arg
                645                 650                 655

Leu Lys Asp Lys Lys Met Asp Ala His Pro Pro Arg Leu Phe Ala Cys
            660                 665                 670

Ser Asn Lys Ile Gly Arg Phe Val Ile Glu Glu Val Pro Gly Glu Leu
            675                 680                 685

Met Gln Glu Asp Leu Ala Thr Asp Asp Val Met Leu Leu Asp Thr Trp
690                 695                 700

Asp Gln Val Phe Val Trp Val Gly Lys Asp Ser Gln Glu Glu Glu Lys
705                 710                 715                 720

Thr Glu Ala Leu Thr Ser Ala Lys Arg Tyr Ile Glu Thr Asp Pro Ala
                725                 730                 735

Asn Arg Asp Arg Arg Thr Pro Ile Thr Val Val Lys Gln Gly Phe Glu
            740                 745                 750

Pro Pro Ser Phe Val Gly Trp Phe Leu Gly Trp Asp Asp Asp Tyr Trp
            755                 760                 765

Ser Val Asp Pro Leu Asp Arg Ala Met Ala Glu Leu Ala Ala
770                 775                 780

<210> SEQ ID NO 2
<211> LENGTH: 372
<212> TYPE: PRT
<213> ORGANISM: Homo sapiens
<220> FEATURE:
<221> NAME/KEY: G1G3
<222> LOCATION: (1)..(372)

<400> SEQUENCE: 2

Met Ala Thr Ala Ser Arg Gly Ala Ser Gln Ala Gly Ala Pro Gln Gly
1               5                   10                  15

Arg Val Pro Glu Ala Arg Pro Asn Ser Met Val Val Glu His Pro Glu
                20                  25                  30
```

Phe Leu Lys Ala Gly Lys Glu Pro Gly Leu Gln Ile Trp Arg Val Glu
            35                  40                  45

Lys Phe Asp Leu Val Pro Val Pro Thr Asn Leu Tyr Gly Asp Phe Phe
 50                  55                  60

Thr Gly Asp Ala Tyr Val Ile Leu Lys Thr Val Gln Leu Arg Asn Gly
 65                  70                  75                  80

Asn Leu Gln Tyr Asp Leu His Tyr Trp Leu Gly Asn Glu Cys Ser Gln
                85                  90                  95

Asp Glu Ser Gly Ala Ala Ala Ile Phe Thr Val Gln Leu Asp Asp Tyr
             100                 105                 110

Leu Asn Gly Arg Ala Val Gln His Arg Glu Val Gln Gly Phe Glu Ser
             115                 120                 125

Ala Thr Phe Leu Gly Tyr Phe Lys Ser Gly Leu Lys Tyr Lys Lys Gly
             130                 135                 140

Gly Val Ala Ser Gly Phe Lys His Val Val Pro Asn Glu Val Val Val
145                 150                 155                 160

Gln Arg Leu Phe Gln Val Lys Gly Arg Arg Val Val Arg Ala Thr Glu
                165                 170                 175

Val Pro Val Ser Trp Glu Ser Phe Asn Asn Gly Asp Cys Phe Ile Leu
                180                 185                 190

Asp Leu Gly Asn Asn Ile His Gln Trp Cys Gly Ser Asn Ser Asn Arg
             195                 200                 205

Tyr Glu Arg Leu Lys Ala Thr Gln Val Ser Lys Gly Ile Arg Asp Asn
             210                 215                 220

Glu Arg Ser Gly Arg Ala Arg Val His Val Ser Glu Glu Gly Thr Glu
225                 230                 235                 240

Pro Glu Ala Met Leu Gln Val Leu Gly Pro Lys Pro Ala Leu Pro Ala
                245                 250                 255

Gly Thr Glu Asp Thr Ala Lys Glu Asp Ala Ala Asn Arg Lys Leu Ala
             260                 265                 270

Lys Leu Tyr Lys Val Ser Asn Gly Ala Gly Thr Met Ser Val Ser Leu
             275                 280                 285

Val Ala Asp Glu Asn Pro Phe Ala Gln Gly Ala Leu Lys Ser Glu Asp
             290                 295                 300

Cys Phe Ile Leu Asp His Gly Lys Asp Gly Lys Ile Phe Val Trp Lys
305                 310                 315                 320

Gly Lys Gln Ala Asn Thr Glu Glu Arg Lys Ala Ala Leu Lys Thr Ala
                325                 330                 335

Ser Asp Phe Ile Thr Lys Met Asp Tyr Pro Lys Gln Thr Gln Val Ser
             340                 345                 350

Val Leu Pro Glu Gly Gly Glu Thr Pro Leu Phe Lys Gln Phe Phe Lys
             355                 360                 365

Asn Trp Arg Asp
    370

<210> SEQ ID NO 3
<211> LENGTH: 344
<212> TYPE: PRT
<213> ORGANISM: Homo sapiens
<220> FEATURE:
<221> NAME/KEY: G4G6
<222> LOCATION: (1)..(344)

```
<400> SEQUENCE: 3

Met Asp Asp Gly Thr Gly Gln Lys Gln Ile Trp Arg Ile Glu Gly
1               5                   10                  15

Ser Asn Lys Val Pro Val Asp Pro Ala Thr Tyr Gly Gln Phe Tyr Gly
            20                  25                  30

Gly Asp Ser Tyr Ile Ile Leu Tyr Asn Tyr Arg His Gly Gly Arg Gln
                35                  40                  45

Gly Gln Ile Ile Tyr Asn Trp Gln Gly Ala Gln Ser Thr Gln Asp Glu
        50                  55                  60

Val Ala Ala Ser Ala Ile Leu Thr Ala Gln Leu Asp Glu Glu Leu Gly
65                  70                  75                  80

Gly Thr Pro Val Gln Ser Arg Val Val Gln Gly Lys Glu Pro Ala His
                85                  90                  95

Leu Met Ser Leu Phe Gly Gly Lys Pro Met Ile Ile Tyr Lys Gly Gly
            100                 105                 110

Thr Ser Arg Glu Gly Gly Gln Thr Ala Pro Ala Ser Thr Arg Leu Phe
            115                 120                 125

Gln Val Arg Ala Asn Ser Ala Gly Ala Thr Arg Ala Val Glu Val Leu
        130                 135                 140

Pro Lys Ala Gly Ala Leu Asn Ser Asn Asp Ala Phe Val Leu Lys Thr
145                 150                 155                 160

Pro Ser Ala Ala Tyr Leu Trp Val Gly Thr Gly Ala Ser Glu Ala Glu
                165                 170                 175

Lys Thr Gly Ala Gln Glu Leu Leu Arg Val Leu Arg Ala Gln Pro Val
            180                 185                 190

Gln Val Ala Glu Gly Ser Glu Pro Asp Gly Phe Trp Glu Ala Leu Gly
        195                 200                 205

Gly Lys Ala Ala Tyr Arg Thr Ser Pro Arg Leu Lys Asp Lys Lys Met
210                 215                 220

Asp Ala His Pro Pro Arg Leu Phe Ala Cys Ser Asn Lys Ile Gly Arg
225                 230                 235                 240

Phe Val Ile Glu Glu Val Pro Gly Glu Leu Met Gln Glu Asp Leu Ala
                245                 250                 255

Thr Asp Asp Val Met Leu Leu Asp Thr Trp Asp Gln Val Phe Val Trp
            260                 265                 270

Val Gly Lys Asp Ser Gln Glu Glu Lys Thr Glu Ala Leu Thr Ser
        275                 280                 285

Ala Lys Arg Tyr Ile Glu Thr Asp Pro Ala Asn Arg Asp Arg Arg Thr
        290                 295                 300

Pro Ile Thr Val Val Lys Gln Gly Phe Glu Pro Pro Ser Phe Val Gly
305                 310                 315                 320

Trp Phe Leu Gly Trp Asp Asp Tyr Trp Ser Val Asp Pro Leu Asp
                325                 330                 335

Arg Ala Met Ala Glu Leu Ala Ala
            340

<210> SEQ ID NO 4
<211> LENGTH: 23
<212> TYPE: DNA
<213> ORGANISM: Artificial sequence
<220> FEATURE:
<221> NAME/KEY: FORWARD_PRIMER
<222> LOCATION: (1)..(23)
<223> OTHER INFORMATION: Forward Primer for amplification of aptamer
      library during different steps of enrichment
```

```
<400> SEQUENCE: 4
tagggaagag aaggacatat gat                                            23

<210> SEQ ID NO 5
<211> LENGTH: 23
<212> TYPE: DNA
<213> ORGANISM: Artificial sequence
<220> FEATURE:
<221> NAME/KEY: REVERSE_PRIMER
<222> LOCATION: (1)..(23)
<223> OTHER INFORMATION: Reverse Primer for amplification of aptamer
      library during different steps of enrichment

<400> SEQUENCE: 5
tcaagtggtc atgtactagt caa                                            23

<210> SEQ ID NO 6
<211> LENGTH: 77
<212> TYPE: DNA
<213> ORGANISM: Artificial sequence
<220> FEATURE:
<221> NAME/KEY: APT_L26F
<222> LOCATION: (1)..(77)
<223> OTHER INFORMATION: Aptamer L26F

<400> SEQUENCE: 6
tagggaagag aaggacatat gatggggcac tgagggtgg gggagcgggg gcggttgact     60
agtacatgac cacttga                                                   77

<210> SEQ ID NO 7
<211> LENGTH: 76
<212> TYPE: DNA
<213> ORGANISM: Artificial sequence
<220> FEATURE:
<221> NAME/KEY: APT_10.10R
<222> LOCATION: (1)..(76)
<223> OTHER INFORMATION: Aptamer 10.10R

<400> SEQUENCE: 7
tcaagtggtc atgtactagt caagcacttt cgctgctcgc tggcgccgcg cccatcatat    60
gtccttctct tccta                                                     76

<210> SEQ ID NO 8
<211> LENGTH: 76
<212> TYPE: DNA
<213> ORGANISM: Artificial sequence
<220> FEATURE:
<221> NAME/KEY: APT_L16F
<222> LOCATION: (1)..(76)
<223> OTHER INFORMATION: Aptamer L16F

<400> SEQUENCE: 8
tagggaagag aaggacatat gataggggga taggaggggg tgggattggg ggattgacta    60
gtacatgacc acttga                                                    76

<210> SEQ ID NO 9
<211> LENGTH: 75
<212> TYPE: DNA
<213> ORGANISM: Artificial sequence
<220> FEATURE:
<221> NAME/KEY: APT_L24F
<222> LOCATION: (1)..(75)
<223> OTHER INFORMATION: Aptamer L24F
```

-continued

```
<400> SEQUENCE: 9
tagggaagag aaggacatat gatcgggggg cgggtattgg gggccggggg gattgactag    60
tacatgacca cttga                                                    75
```

APTAMERS FOR PURIFYING AND QUANTIFYING GELSOLIN AND ITS VARIANTS

CROSS-REFERENCE TO RELATED APPLICATIONS

This application is a National Stage of International Application No. PCT/IN2015/050128, filed Oct. 5, 2015, which claims priority to Indian Patent Application No. 2852/DEL/2014, filed on Oct. 7, 2014. The disclosure of the above application is incorporated herein by reference.

FIELD OF THE INVENTION

The present invention relates to novel DNA aptamers capable of specifically binding to gelsolin with high affinity and utilizing this property of these aptamers to estimate the gelsolin levels in a given sample and purify bulk quantities of tagless gelsolin and its variants. Currently, estimation of gelsolin levels in a sample utilizes either actin as a gelsolin binding protein or anti-gelsolin antibodies. Actin is extracted primarily from rabbit or chicken muscle tissue. Similarly, antibodies production also involves either mammalian cell culture or the use of animals including rabbit, mouse, goat, llama, horse, hen etc. Thus, the present invention attempts to diagnose and purify plasma gelsolin levels using small DNA molecules; thereby eliminating the use of different animals/their tissues to produce gelsolin binding proteins, which are much more expensive and socially unacceptable methods as opposed to the synthesis of a DNA molecule by in vitro PCR. These aptamers can be chemically synthesized and/or biochemically generated using PCR and/or produced by bacteria using simple molecular biology tools and protocols. Using this strategy, bulk production of the gelsolin binding matrix can be carried out at much lower cost.

BACKGROUND OF THE INVENTION AND DESCRIPTION OF PRIOR ART

Gelsolin is a six-domain (G1-G6) multifunctional actin assembly regulator protein. It exists as three isoforms in humans which include two cytoplasmic and one extracellular isoform secreted into plasma. All these isoforms are encoded by a single gene located on chromosome 9 in humans. The major functions of cytoplasmic gelsolin involve actin depolymerization as well as nucleation primarily regulated by calcium, pH and phosphoinositides (Ashish et al, 2007; Garg et al, 2011; Peddada et al, 2013). To initiate polymerization, it binds to two globular actin monomers (G-actin) and to affect actin depolymerization function, it binds to filamentous actin (F-actin), severs the filament by weakening non-covalent bonds between the actin monomers and remains attached to the barbed end of filament as a cap to prevent subsequent elongation (Yin & Stull, 1999).

In plasma, gelsolin is primarily involved in the rapid severing and removal of actin filaments released from dead cells into the blood stream. Plasma gelsolin [pGSN] thus serves a protective role by clearing toxic circulating filamentous-actin released in blood due to cell necrosis (Lee & Galbraith, 1992). In addition, plasma gelsolin also has the ability to bind to a variety of proinflammatory and bioactive molecules including lyso-phosphatidic acid, sphingosine 1-phosphate, fibronectin and platelet activating factor in the body which act as mediators of many physiological functions including wound healing, neurologic development, cancer progression and angiogenesis (Bucki et al, 2010; Lind & Janmey, 1984; Lind et al, 1988; Osborn et al, 2007). pGSN has been suggested to thus sequester these bioactive mediators of inflammation and localize inflammatory and immune reactions to the sites of injury. Apart from these bioactive molecules, pGSN has the ability to bind to the bacterial surface lipids, lipoteichoic acid (LTA) and lipopolysaccharide, (LPS) which belong to Gram-positive and Gram-negative bacteria, respectively (Bucki et al, 2008; Bucki et al, 2005). This interaction compromises the ability of LTA and LPS to mediate innate immune responses in the host (Bucki et al, 2008).

Human plasma gelsolin circulates in blood at a concentration of ~200 µg/ml (Osborn et al, 2008). Clinical significance and the therapeutic importance of this protein have been well illustrated in animal models as well as in patients with various diseases. A significant decrement (20-50%) in plasma gelsolin levels has been documented in a variety of illnesses or health complications which include major to minor trauma, burn, acute respiratory distress syndrome (ARDS), acute lung injury, acute liver injury, surgery, sepsis, hepatitis, malaria, MODS (including myocardial infarction, septic shock and myonecrosis), allogenic stem cell transplantation, and multiple sclerosis (Peddada et al, 2012). Moreover, the plasma gelsolin levels have been found to be increasing in patients recovering from the diseases. Furthermore, it has been confirmed that repletion with exogenous recombinant gelsolin significantly increases the survival rate in animal models of different acute insults (Lee et al, 2007).

On the whole, all these studies aimed at investigating the correlation of pGSN level with the severity of health problem as well as clinical outcomes suggest that: 1) pGSN level declines after a cellular injury either due to surgery, inflammation or infection and this decline correlates very well with the extent of cellular injury, 2) pGSN levels declining below a critical level greatly enhance the risk of mortality, thus based upon the admission pGSN levels, exogenous gelsolin could be administered in the patients, having critically low pGSN levels, to improve their chances of survival. Thus, pGSN holds an immense potential as an excellent prognostic biomarker for multiple health conditions as well as a therapeutically relevant protein to improve the patient's health status.

However, without knowing the exact plasma gelsolin levels of healthy individuals as well as the patient, gelsolin replacement therapy can not be a reality. Existing commercial kits for the estimation of gelsolin levels in a given sample use the method of sandwich ELISA [enzyme linked immunosorbent assay]. Briefly, gelsolin specific antibodies are coated onto the ELISA plates, these are then used for the binding of gelsolin present in standards and test samples. The bound gelsolin is then detected by using a biotin labeled anti-gelsolin antibody and streptavidin-horse radish peroxidase conjugate. Nevertheless, all these kits are intended for research use only and not for diagnostic purposes.

In short, it may be summarized that till now, no affordable, accurate and accelerated diagnostic method exists in the literature, which can be reliably used for the determination of plasma gelsolin levels of humans and other animals. Considering the emerging need to measure plasma gelsolin levels in different disease or stress conditions and therapeutic potential of injecting exogenous gelsolin and/or its forms to improve patient condition, the role of aptamers in quantifying and purifying gelsolin and its variants holds great translation potential and has not been reported till date.

OBJECTS OF THE INVENTION

The main object of the present invention is thus to provide novel and specific DNA aptamers exhibiting gelsolin binding property and which are useful for developing protocols of quantifying and/or purifying gelsolin and its variants.

Another object of the present invention is to provide a process for the estimation of gelsolin levels in a sample by using the novel invented DNA aptamers and their modified versions.

Still another object of the present invention is to provide diagnostic kits for the estimation of gelsolin levels in a sample.

Yet another object of the present invention is to provide novel DNA aptamers and their modified versions useful in developing/generating affinity matrix for purifying gelsolin and its variants including tagless ones.

A further object of the present invention is to provide a process whereby the claimed DNA aptamers can specifically and tightly bind to gelsolin, thereby blocking ability of gelsolin to bind other proteins.

SUMMARY OF THE INVENTION

The present invention relates to the identification and utilization of gelsolin binding DNA aptamers for estimating the gelsolin levels in a given sample, and purifying tagged or tagless gelsolin and its variants.

Overcoming the limitations of batch to batch variation in samples of antibodies and actin useful for the preparation of gelsolin identification kit(s) or protocol(s), a random DNA aptamer library was screened to identify the aptamers capable of binding gelsolin [NCBI Reference Sequence: NP_000168.1] (SEQ ID NO: 1) or its N- and C-terminal halves, namely G1-G3 and G4-G6 (SEQ ID NO: 2 and 3, respectively). The oligonucleotides [aptamers] were synthesized by PCR, purified and their ability to bind gelsolin and its variants was tested experimentally. Results brought forth that some DNA aptamers bind gelsolin and its variants with specificity and sensitivity comparable to anti-gelsolin antibodies (IgG or IgY) and actin. The high point of this process is that DNA aptamers can be produced easily by PCR protocols and extracted at a high degree of purity. Also the concentration of DNA aptamers, which are relatively more stable than proteins, can be regulated with high precision. This feature will prove beneficial in using DNA aptamers as a coating or binding material in gelsolin diagnostic kit(s), and/or generating affinity matrix to bulk purify tagless gelsolin and its versions. Considering the emerging need to measure plasma gelsolin levels in different disease or stress conditions, and therapeutic potential of injecting exogenous gelsolin and/or its forms to improve patient condition, the role of aptamers in quantifying and purifying gelsolin and its variants holds great translation potential and has not been reported till date.

In an embodiment of the present invention, the property of binding of the DNA aptamers to gelsolin is used as a tool in developing applications for quantification of gelsolin levels in samples including those from humans and/or animals. This property can well be extended to develop gelsolin related diagnostic kit(s).

In another embodiment of the present invention, the property of binding of aptamers to gelsolin is used as a tool in developing applications for purification of gelsolin and its variants from a mixture.

In yet another embodiment of the present invention, the gelsolin binding property of aptamers is used to functionalize a stationary phase matrix used in chromatography to develop an affinity chromatography protocol for bulk purification of gelsolin and its variants.

In still another embodiment of the present invention, the property of aptamers to specifically and tightly bind gelsolin has been employed to block functioning of gelsolin in undesirable pathways, leading to therapeutic potential of these aptamers.

Sequences of different DNA aptamers capable of binding gelsolin are submitted in the SEQUENCE LISTING.txt and are mentioned in the table below along with other sequences used in the invention:

| SEQ ID No: | Sequence type | Sequence |
|---|---|---|
| 1 | Human Gelsolin Mature Protein [NCBI Reference Sequence: NP_000168.1] [Protein] Named-Gelsolin Abbreviation-GSN | MAPHRPAPALLCALSLALCALSLPVRAATASRGAS QAGAPQGRVPEARPNSMVVEHPEFLKAGKEPGLQI WRVEKFDLVPVPTNLYGDFFTGDAYVILKTVQLRN GNLQYDLHYWLGNECSQDESGAAAIFTVQLDDYLN GRAVQHREVQGFESATFLGYFKSGLKYKKGGVASG FKHVVPNEVVVQRLFQVKGRRVVRATEVPVSWESF NNGDCFILDLGNNIHQWCGSNSNRYERLKATQVSK GIRDNERSGRARVHVSEEGTEPEAMLQVLGPKPAL PAGTEDTAKEDAANRKLAKLYKVSNGAGTMSVSLV ADENPFAQGALKSEDCFILDHGKDGKIFVWKGKQA NTEERKAALKTASDFITKMDYPKQTQVSVLPEGGE TPLFKQFFKNWRDPDQTDGLGLSYLSSHIANVERV PFDAATLHTSTAMAAQHGMDDDGTGQKQIWRIEGS NKVPVDPATYGQFYGGDSYIILYNYRHGGRQGQII YNWQGAQSTQDEVAASAILTAQLDEELGGTPVQSR VVQGKEPAHLMSLFGGKPMIIYKGGTSREGGQTAP ASTRLFQVRANSAGATRAVEVLPKAGALNSNDAFV LKTPSAAYLWVGTGASEAEKTGAQELLRVLRAQPV QVAEGSEPDGFWEALGGKAAYRTSPRLKDKKMDAH PPRLFACSNKIGRFVIEEVPGELMQEDLATDDVML LDTWDQVFVWVGKDSQEEEKTEALTSAKRYIETDP ANRDRRTPITVVKQGFEPPSFVGWFLGWDDDYWSV DPLDRAMAELAA |
| 2 | N-terminal half of gelsolin [Protein] Named-G1-G3 Abbreviation-G1-G3 | MAPHRPAPALLCALSLALCALSLPVRAATASRGAS QAGAPQGRVPEARPNSMVVEHPEFLKAGKEPGLQI WRVEKFDLVPVPTNLYGDFFTGDAYVILKTVQLRN GNLQYDLHYWLGNECSQDESGAAAIFTVQLDDYLN GRAVQHREVQGFESATFLGYFKSGLKYKKGGVASG |

| SEQ ID No: | Sequence type | Sequence |
|---|---|---|
| | | FKHVVPNEVVVQRLFQVKGRRVVRATEVPVSWESF NNGDCFILDLGNNIHQWCGSNSNRYERLKATQVSK GIRDNERSGRARVHVSEEGTEPEAMLQVLGPKPAL PAGTEDTAKEDAANRKLAKLYKVSNGAGTMSVSLV ADENPFAQGALKSEDCFILDHGKDGKIFVWKGKQA NTEERKAALKTASDFITKMDYPKQTQVSVLPEGGE TPLFKQFFKNWRD |
| 3 | C-terminal half of gelsolin [Protein] Named-G4-G6 Abbreviation-G4-G6 | MDDDGTGQKQIWRIEGSNKVPVDPATYGQFYGGDS YIILYNYRHGGRQGQIIYNWQGAQSTQDEVAASAI LTAQLDEELGGTPVQSRVVQGKEPAHLMSLFGGKP MIIYKGGTSREGGQTAPASTRLFQVRANSAGATRA VEVLPKAGALNSNDAFVLKTPSAAYLWVGTGASEA EKTGAQELLRVLRAQPVQVAEGSEPDGFWEALGGK AAYRTSPRLKDKKMDAHPPRLFACSNKIGRFVIEE VPGELMQEDLATDDVMLLDTWDQVFVWVGKDSQEE EKTEALTSAKRYIETDPANRDRRTPITVVKQGFEP PSFVGWFLGWDDDYWSVDPLDRAMAELAA |
| 4 | Forward Primer [DNA] for amplification of aptamer library during different steps of enrichment | tagggaagagaaggacatatgat |
| 5 | Reverse Primer [DNA] for amplification of aptamer library during different steps of enrichment | tcaagtggtcatgtactagtcaa |
| 6 | Aptamer L26F (77 bases) [DNA] | tagggaagagaaggacatatgatggggcac tggagggtgggggagcggggcggttgact agtacatgaccacttga |
| 7 | Aptamer 10.10R (76 bases) [DNA] | tcaagtggtcatgtactagtcaagcacttt cgctgctcgctggcgccgcgcccatcatat gtccttctcttcccta |
| 8 | Aptamer L16F (76 bases) [DNA] | tagggaagagaaggacatatgatagggga taggaggggtgggattgggggattgacta gtacatgaccacttga |
| 9 | Aptamer L24F (75 bases) [DNA] | tagggaagagaaggacatatgatcgggggg cgggtattgggggccggggggattgactag tacatgaccacttga |

BRIEF DESCRIPTION OF THE ACCOMPANYING DRAWINGS

FIG. 1 illustrates the flow chart depicting the strategy of aptamer library screening to identify specific aptamers with binding ability to gelsolin. This protocol was followed to enrich the aptamers capable of binding gelsolin.

Figure 2:
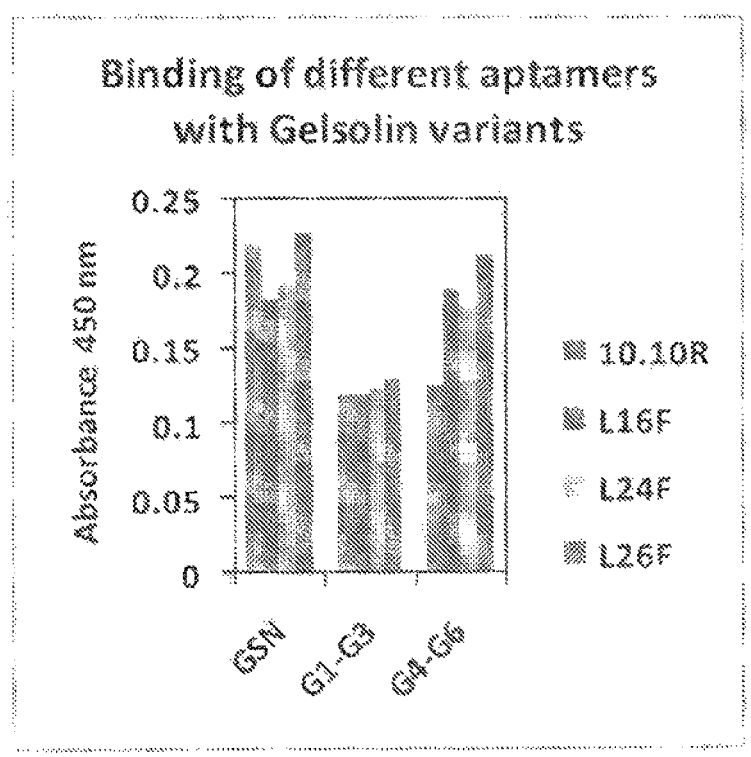

FIG. 2 illustrates the binding ability of different aptamers with gelsolin (GSN) and its two variants/halves (G1-G3 and G4-G6) (SEQ ID No: 1, 2 and 3, respectively). The binding abilities of different aptamers coated onto 96 well ELISA plate with recombinant gelsolin as determined by microtiter binding assay are shown. Main result conveyed by this figure is that gelsolin (GSN), G1-G3, and G4-G6 can bind to all the claimed aptamers.

Figure 3:
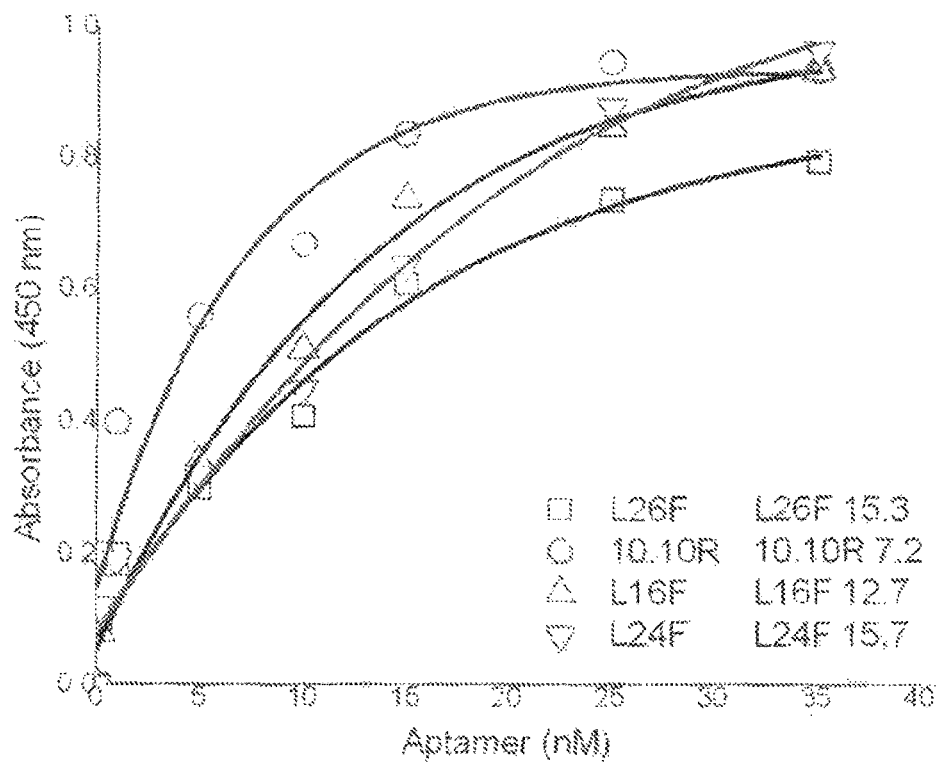

FIG. 3 illustrates the binding affinity of aptamers for gelsolin. The gelsolin binding affinities of aptamers were calculated from the binding curve of aptamers coated at different concentrations with a fixed concentration of gelsolin as determined by microtiter binding assay. X-axis denotes the concentration of the aptamers claimed in nM (nanomolars), and the Y-axis is absorbance of the reaction mixture observed experimentally at 450 nm (nanometers). The legends □, Δ, ○ and ∇ denote the datapoint with respect to the concentration of the aptamer used. The number value next to the aptamer indicates the binding constant ($K_d$) of the aptamer to gelsolin (GSN). Thus, the results are L26F, 10.10R, L16F and L24F individually bind to gelsolin with an estimated $K_d$ of 15.3, 7.2, 12.7 and 15.7 nM.

Figure 4:
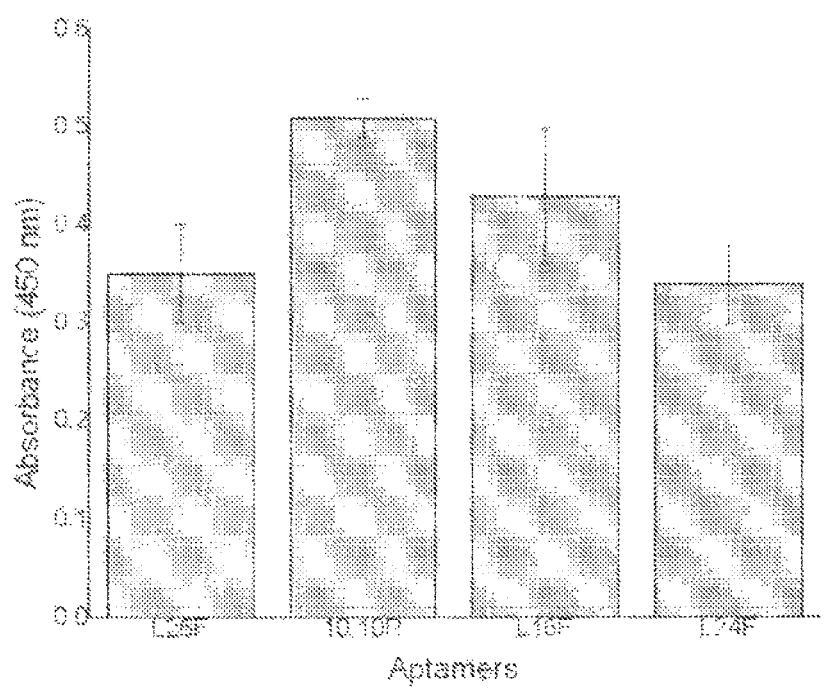

FIG. 4 illustrates the binding of aptamers with immobilized gelsolin. Recombinant gelsolin was coated onto ELISA plate and was allowed to bind to biotin labeled aptamers. The bound aptamers were then detected using streptavidin-horseradish peroxidase conjugate. The graph shows the binding of selected aptamers with immobilized gelsolin. It is evident that the claimed aptamers can bind immobilized gelsolin where L26F, L24F bind with similar efficacy, and 10.10R is best in relative binding with L16F having in-between relative capability. These results are in correlation with binding constant results provided in FIG. 3.

Figure 5:
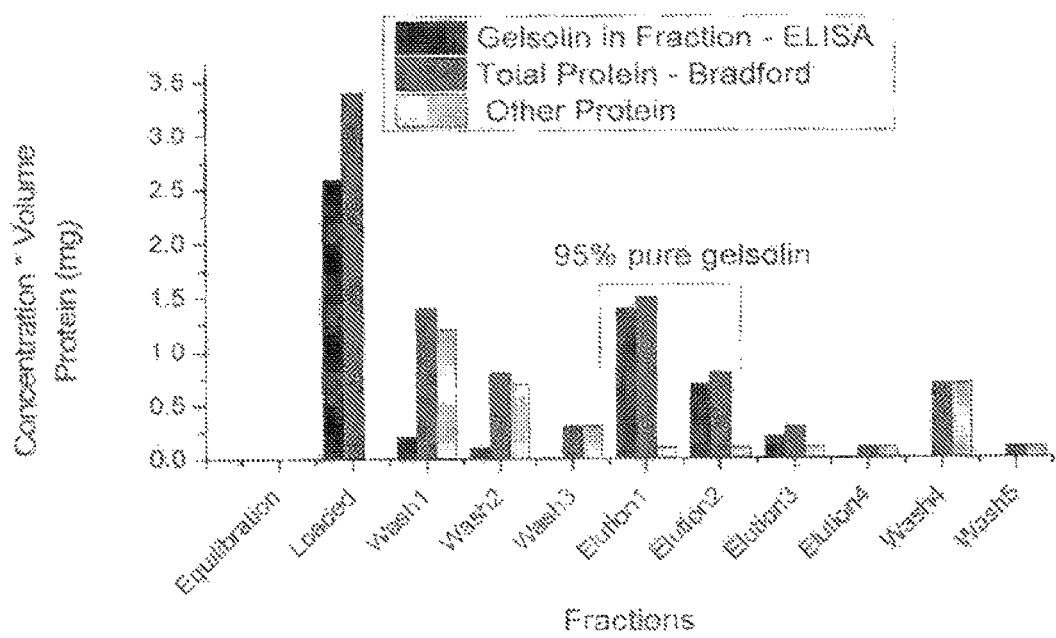

FIG. 5 illustrates the purification of Gelsolin using selected aptamers bound to Sepharose. Results confirm that using the claimed aptamers and the protocol described in detail, one can purify gelsolin (GSN) with 95% or higher purity.

Figure 6:
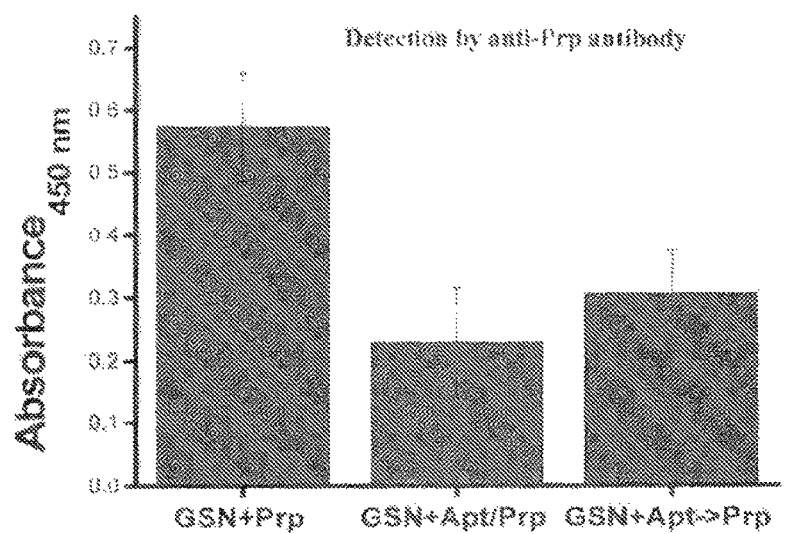

FIG. 6 illustrates that the selected aptamers bind to immobilized gelsolin (GSN) and does not allow it to bind Prion causing Prp protein. GSN+Prp indicates addition of Prion Prp protein (Prp) to gelsolin (GSN) immobilized on ELISA plate via coated anti-gelsolin monoclonal antibody; GSN+Apt/Prp indicates addition of mixture of Prp and one of the claimed aptamer to immobilized gelsolin; GSN+Apt→Prp indicates addition of Prp first, followed by one of the claimed aptamer to immobilized gelsolin. Detection of bound Prp was done using anti-Prp rabbit antibodies followed by secondary antibodies to rabbit antibodies.

LIST OF ABBREVIATIONS USED

| | |
|---|---|
| GSN | Human Gelsolin Protein |
| pGSN | Plasma Gelsolin |
| PBS | phosphate buffered saline |
| G1-G3 | N-terminal half of gelsolin protein |
| G4-G6 | C-terminal half of gelsolin protein |
| Prp | Recombinant Prion Protein, Prp |
| Apt | Aptamer |
| ELISA | Enzyme linked immunosorbent assay |
| EGTA | ethylene glycol tetraacetic acid |
| TMB | 3,3',5,5'-Tetramethylbenzidine |
| SELEX | Systematic Evolution of Ligands by Exponential Enrichment |
| DEAE | Diethylaminoethyl cellulose |
| GST | Glutathione S-transferase |
| MBP | Maltose binding protein |

DETAILED DESCRIPTION OF THE INVENTION

Reduced levels of plasma gelsolin have been reported in various diseases and repletion of exogenous gelsolin has shown improvement in animal models of burn and sepsis. It is anticipated that in future gelsolin levels will be examined in a number of medical cases. Possibly, recombinant gelsolin and its functional variants will be used for therapeutic purposes. Thus, it is imperative to provide novel entities which can bind to gelsolin as well as develop plasma gelsolin diagnostic kit(s) and ways to express and purify gelsolin and its versions. Novel DNA aptamers which can bind tightly and specifically to gelsolin will help in developing ways to quantify and purify gelsolin and its variants, and block functioning of gelsolin in undesirable pathways, thus projecting a potential therapeutic role of these aptamers. Here, we demonstrate that these aptamers bind gelsolin and stop gelsolin mediated prion protein association.

Present invention describes novel DNA aptamers and use thereof as gelsolin binding molecules. The present invention for the first time reports specific aptamers which are capable of binding to gelsolin.

Aptamers are short DNA/RNA/peptide molecules which can bind specifically to a target molecule (Pan & Clawson, 2009). These are usually identified by Systematic Evolution of Ligands by Exponential Enrichment (SELEX). SELEX method involves exposing a random sequence library to a specific target and amplifying the bound molecules which are then subjected to additional rounds of selection. After multiple rounds of selection, specific aptamers identified for binding to the target molecule are subjected to different modifications to improve their binding affinity and stability.

Gelsolin is a calcium dependent, multifunctional actin regulatory protein composed of six domains (G1-G6), which appear to have arisen from a triplication event followed by a duplication of an ancestral gene encoding a single domain (Kwiatkowski et al, 1986; Osborn et al, 2008). It exists as three isoforms, two cytoplasmic and a secreted extracellular plasma isoform, all encoded by a single gene located on chromosome 9 in humans. This single gene is subjected to alternative transcriptional initiation and splice site selection in different tissues resulting in differences at the amino termini of the isoforms (Kwiatkowski et al, 1988; Yin et al, 1984). Mature plasma (secreted) gelsolin (plasma GSN, formed after cleavage of 27 residue amino-terminal signal sequence) differs from its cytoplasmic counterpart by an additional unique leader peptide (24 amino acids) at its N-terminal (Kwiatkowski et al, 1986) and presence of a disulfide bond providing additional stability (Wen et al, 1996). The rest of the polypeptide is identical in sequence to the cytoplasmic form (Kwiatkowski et al, 1986). The third minor isoform called gelsolin-3 is a non-secreted form containing an additional 11 amino acids at the N terminus as compared to the cytoplasmic counterpart. While cytoplasmic gelsolin gets expressed in a wide range of tissues, gelsolin-3 expresses predominantly in oligodendrocytes in the brain, lungs and testis and, is involved in myelin remodeling during spiralization around the axon (Vouyiouklis & Brophy, 1997). Plasma GSN is mainly produced and secreted into blood by muscle cells (Kwiatkowski et al, 1988).

Clinical significance and the therapeutic importance of plasma gelsolin have been well illustrated in animal models as well as in patients with various diseases. A significant decrement in pGSN levels has been documented in a variety of illnesses ranging from minor/major trauma, infections to chronic inflammation (Peddada et al, 2012). Patients with low pGSN levels were observed to have higher mortality rate, longer hospital stay and longer ventilation time in intensive care units as compared to healthy controls. pGSN levels were found to be increasing in patients recovering from diseases. Furthermore, it has been confirmed that repletion with exogenous recombinant pGSN significantly increases the survival rate in animal models of different acute insults (Lee et al, 2007). However, without knowing the exact plasma gelsolin levels of healthy individuals as well as the patient, gelsolin replacement therapy cannot become a reality. Till date, no "diagnostic method" exits in the literature, and kits/protocols based on these aptamers can be reliably used for the determination of plasma gelsolin levels of humans and other animals for clinical uses.

The term "diagnostic" as used in above embodiment refers to the process/method of determining the value of a given entity which could help in finding out the reason/ extent of a clinical condition and thus is of clinical use as well as for research purposes.

The phrase "given sample" as used in above embodiment refers to any biological sample which includes but is not limited to blood, serum, plasma, urine, saliva obtained from human or other animals.

The phrase "Plasma gelsolin" as used in above embodiment refers to the gelsolin present in plasma sample of human or other animals.

The phrase "Plasma gelsolin" as used above refers to the gelsolin present in human/animal plasma which could be a mixture of plasma isoform and other isoforms of gelsolin released into blood due to cell necrosis.

Plasma isoform of gelsolin is the isoform of gelsolin (protein) which gets secreted into blood mainly from muscle cells.

The phrase "clinical use" refers to the purpose of knowing the gelsolin levels in a given human/animal sample in order to determine the best treatment strategy for the human/ animal from which the "sample" was obtained.

The term "treatment" as used herein refers to an approach for obtaining beneficial or desired result including clinical results. Beneficial or desired clinical results can include but are not limited to alleviation or amelioration of one or more symptoms or conditions, diminished extent of disease, stabilization of state of disease, slowing disease progression and also prolonging survival as compared to expected survival in the absence of treatment.

The term "functionalize" as used herein refers to covalent binding of DNA aptamers on silica/modified silica/agarose/sepharose beads by chemical reaction.

The term "affinity chromatography" as used herein refers to binding and thus retention of gelsolin in mobile phase on the aptamers in the stationary phase of the chromatography protocol.

Accordingly the main embodiment of the present invention provides novel DNA aptamers represented by SEQ ID Nos. 6 to 9.

Another embodiment of the present invention provides DNA aptamers as herein described capable of binding the protein gelsolin represented by SEQ ID No. 1 or its variants represented by SEQ ID No. 2 and 3.

Another embodiment of the present invention provides DNA aptamers as herein described useful for the quantification of gelsolin levels in a sample.

Another embodiment of the present invention provides a method for the quantification of gelsolin in a sample using the aptamers as herein described, wherein the steps comprise:

[a] coating 1 ug of streptavidin on a support using 100 mM NaHCO$_3$ buffer having pH 9.2 for 10 to 12 hours at a temperature of 4 degree C.;

[b] washing the coated support of step [a] with PBS and blocking with 3% BSA in PBS for 2 hours followed by washing with PBS;

[c] immobilizing 2 uM of the biotin labeled aptamer selected from SEQ ID Nos. 6 to 9 on the support of step [b] using TE buffer having pH 8 supplemented with 2M NaCl for 2 hours at room temperature;

[d] washing the coated support of step [c] 2 times with PBS containing 0.1% Tween-20;

[e] adding gelsolin in the range of 0.2 uM-5 nM or a sample diluted in selection buffer containing 0.1% BSA to the support of step [d] and allowing to stand for 2 hours;

[f] washing the coated support of step [e] 4 times with PBS containing 0.1% Tween-20 followed by adding anti-gelsolin antibodies and incubating for 10 to 12 hours at 4 degree C.;

[g] washing the support obtained in step [f] 4 times with PBS containing 0.1% Tween-20 followed by adding secondary antibodies conjugated with horseradish peroxidase and incubating for 1 hour and then adding the substrate for horseradish peroxidase;

[h] terminating the reaction of step [g] with 2M H$_2$SO$_4$ after the development of blue colour and measuring the absorbance at 450 nm so as to determine the quantity of gelsolin present in the sample.

Yet another embodiment of the present invention provides a method for the quantification of gelsolin in a sample using the aptamers as herein described, wherein the steps comprise:

[a] coating anti-gelsolin antibodies on a support using 100 mM NaHCO$_3$ buffer having pH 9.2 for 10 to 12 hours at a temperature of 4 degree C.;

[b] washing the coated support of step [a] with PBS and blocking with 3% BSA in PBS for 2 hours followed by washing with PBS;

[c] adding gelsolin in the range of 0.2 uM-5 nM or a sample diluted in PBS containing 0.1% BSA and 0.01% Tween-20 to the support of step [b] and allowing to stand for 2 hours at room temperature;

[d] washing the coated support of step [c] 3 times with PBS containing 0.1% Tween-20;

[e] adding 1 uM of the biotin labeled aptamer selected from SEQ ID Nos. 6 to 9 diluted in selection buffer containing 0.1% BSA to the support of step [d] and allowing to stand for 2 hours;

[f] washing the coated support of step [e] 4 times with PBS containing 0.1% Tween-20 followed by adding streptavidin conjugated with horseradish peroxidase and incubating for 1 hour and then adding the substrate for horseradish peroxidase;

[g] terminating the reaction of step [f] with 2M H$_2$SO$_4$ after the development of blue colour and measuring the absorbance at 450 nm so as to determine the quantity of gelsolin present in the sample.

Yet another embodiment of the present invention provides DNA aptamers as herein described, useful for the purification of gelsolin from a mixture.

A method for the purification of gelsolin from a mixture using the aptamers as herein described, wherein the steps comprise:

[a] washing the CNBr activated Sepharose beads with ice-cold double-distilled water and adding 10 mM potassium phosphate (pH 8) and 5'-phosphorylated oligos thereto to make a thick slurry of the activated beads;

[b] stirring the slurry obtained in step [a] at room temperature for 14 hours and washing with 1 M potassium phosphate (pH 8) containing 1 M KCl;

[c] washing the beads obtained in step [b] with water, followed by resuspending in 10 mM Tris-HCl (pH 8) containing 300 mM NaCl, 1 mM EDTA;

[d] pouring the slurry of beads obtained in step [c] in a PD-10 column and washing with three column volumes of 40 mM Tris buffer pH 8 containing 100 mM NaCl and 2 mM EGTA;

[e] adding to the column obtained in step [d], the cell lysate containing gelsolin with pH adjusted to pH 8 and containing 2 mM EGTA;

[f] washing the column of step [e] obtained after initial loading with three column volumes of 40 mM Tris buffer pH 8 containing 100 mM NaCl and 3 mM CaCl$_2$;

[g] eluting the bound gelsolin from the column of step [f] by adding 40 mM Tris buffer pH 8 containing 300 mM of NaCl and 20 mM of CaCl$_2$.

Another embodiment of the present invention provides a kit for the detection of gelsolin using the aptamers as herein described, wherein the kit comprising:

[a] a solid phase having immobilized thereon the aptamer selected from SEQ ID Nos. 6 to 9;

[b] sample containing gelsolin;

[c] detection reagents containing anti-gelsolin antibodies and secondary antibodies conjugated with horseradish peroxidase which are capable of detecting the presence of gelsolin.

EXAMPLES

The following examples are given by way of illustration and therefore should not be construed to limit the scope of the present invention.

Example 1: Identification of Gelsolin Binding DNA Aptamers

Production of Recombinant Gelsolin and its Variants:

The amplified product of cDNA clone obtained from NIH Mammalian Gene Collection-Human gene clone ID 4661084 was digested with XbaI and XhoI, and subcloned into the vector backbone of pET303/CT-His (Invitrogen, NY, USA). The gelsolin variants were generated by site-directed or deletion mutagenesis as previously described (Peddada et al, 2013). The sequences of subcloned gelsolin DNA were verified by automated DNA sequencing (Applied Biosystems, USA). The plasmids thus created were used to transform *E. coli* BL21 (DE3) which was commercially procured from M/s Invitrogen, USA vide catalogue number C6000-03, for the heterologous protein expression. The transformed bacteria carrying pET303/Gelsolin and its mutants were deposited with MTCC, Chandigarh, India an International Depository Authority recognized under the Budapest treaty vide Accession number MTCC5885 on Sep. 1, 2014. The bacteria MTCC 5885 were grown in LB broth (Merck, Germany) to a density of $OD_{600}=0.5$ followed by induction of recombinant protein expression with 1 mM isopropyl-β-D-thiogalactoside (IPTG) for 4-5 additional hours. The expressed proteins were purified by weak anion exchange chromatography (DE-52). The target protein was immobilized onto CNBr activated sepharose beads as follows.

Coupling of the Affinity Material to the Sepharose Beads:

Proteins (BSA and gelsolin) were dialyzed against the 100 mM $NaHCO_3$, pH 9.0 buffer and concentration was estimated by measuring the absorbance at 280 nm. CNBr activated resin was allowed to swell in 1 mM HCl for 15 min at room temperature and then equilibrated with coupling buffer (100 mM $NaHCO_3$, pH 9.0). After equilibration, the resin was immediately transferred to protein solution and incubated with agitation overnight at 4° C. Beads were collected by centrifugation at 2000×g for 1 min and the protein concentration of the supernatant was determined (it should be 10-fold less than what was observed at step 1). The beads were washed 3-4 times with coupling buffer and then incubated with blocking buffer containing 1 M ethanolamine in coupling buffer for 2 hrs at room temperature. After incubation, beads were washed 4 times with a combination of low pH and high pH buffer and finally with 1×PBS containing 0.01% sodium azide.

Screening to Identify the Aptamers against the Recombinant Gelsolin and its Variants:

Briefly, 2 nmol library of 76 b oligonucleotides including a central random nucleotide region of 30-mer (TriLink Biotechnologies, CA, USA), representing $10^{18}$ unique sequences was diluted in selection buffer (25 mM Tris-HCl, pH 8, 150 mM NaCl, 2 mM $CaCl_2$, 5 mM $MgCl_2$ and 10 mM KCl and 0.01% Tween20) and incubated at 94° C. for 5 min and kept in ice for 10 min followed by an incubation of 20 min at room temperature. The DNA was then allowed to bind to the target protein (GSN) conjugated sepharose beads for 1 hr at room temperature. Resulting DNA eluted after selection was purified by phenol-chloroform extraction, ethanol precipitated and resuspended in 10 uL TE (10 mM Tris-HCl, pH 8, 1 mM EDTA). The DNA was PCR amplified in two 50 uL reaction mixtures containing 2.5 U of Taq DNA polymerase, 1× Taq buffer with $(NH4)_2SO_4$, 0.5 uM of both selection primers (SEQ ID Nos. 4 and 5), 2.5 mM $MgCl_2$, 0.2 mM dNTP and 2.5 uL of template. Amplification conditions were 2 min at 94° C.; 15 cycles of 10 s at 94° C., 10 s at 62° C., 10 s at 72° C.; 2 min at 72° C. 90 uL of amplified DNA was first subjected to negative selection using BSA conjugated sepharose beads and then incubated with gelsolin conjugated beads as earlier. After ten rounds of this SELEX method (FIG. 1), enriched aptamer library was subcloned using TOPO-TA cloning kit (Invitrogen, NY, USA). The subcloned aptamers were subjected to automated DNA sequencing and the individual aptamers were amplified by PCR as above for verification of the ability to bind gelsolin and variants by microtiter binding assays.

Example 2: Microtiter Binding Assay

The binding ability of the aptamers described herein (L26F, 10.10R, L16F and L24F) with recombinant gelsolin and its N- and C-terminal halves [represented by SEQ ID No. 2 and 3, respectively] was estimated using microtiter binding assay (FIG. 2). (The sequences of gelsolin binding aptamers are represented by SEQ ID Nos. 6-9.) Briefly, different aptamers (100 nM) or actin (100 nM) extracted from chicken muscle (Peddada et al, 2013) were coated on to 96 well ELISA plates in TE (10 mM Tris-HCl, pH 8, 1 mM EDTA) supplemented with 30% ammonium sulfate and 100 mM $NaHCO_3$ buffer, pH 9.2 respectively overnight at 4° C. The wells were washed with PBS and blocked with 300 uL per well of 3% BSA in phosphate buffered saline [PBS] for 2 hrs at room temperature. The wells were washed with PBS and were allowed to bind to 100 nM gelsolin diluted in selection buffer for 2 hrs at room temperature. The wells were then washed 4 times with PBS containing 0.1% Tween20 (PBS-T) and incubated with anti-gelsolin antibodies overnight at 4° C. The plates were washed 4 times with PBS-T and incubated with secondary antibodies conjugated with horseradish peroxidase at room temperature for 30 min followed by detection using 1-step Ultra TMB substrate (Pierce, Rockford, USA). The reactions were stopped with stop solution (2 M $H_2SO_4$) after the blue color had developed and absorbance was read at 450 nm using a microplate reader.

Example 3: Determination of Affinity of Aptamers for Gelsolin

To determine the affinity of different aptamers for gelsolin, 1 ug of streptavidin was coated on a support using 100 mM $NaHCO_3$ buffer having pH 9.2 for 10 to 12 hours at a temperature of 4 degree C. The wells were washed with PBS and blocked with 3% BSA in PBS for 2 hours followed by washing with PBS. The aptamers, L26F (SEQ ID NO: 6), 10.10R (SEQ ID NO: 7), L16F (SEQ ID NO: 8) and L24F (SEQ ID NO: 9) were immobilized at a concentration range of 100 nM-1.56 nM on to ELISA plates using Tris-EDTA, pH 8 supplemented 2M NaCl for 2 hrs. The wells were washed with PBS containing 0.1% Tween 20 and were allowed to bind to 100 nM gelsolin diluted in selection buffer for 2 hrs at room temperature. After washing the bound gelsolin was detected using anti-gelsolin antibodies and secondary antibodies using standard procedures as above. Using non linear curve fitting of the plots (FIG. 3), the dissociation constant, $K_d$, values of L26F, 10.10R, L16F and L24F for binding to gelsolin were calculated to be 15.3, 7.2, 12.7 and 15.7 nM, respectively. Similar results were obtained upon using hydrophobic and/or hydrophilic surface containing ELISA plates, confirming equal efficacy of the immobilized aptamers to bind gelsolin and its variants from the solution.

Example 4: Binding of Aptamers with Immobilized Gelsolin

Recombinant gelsolin was coated at a concentration of 1.56 nM on to ELISA plate in 100 mM $NaHCO_3$ buffer, pH 9.2 at 4° C. overnight. The wells were washed with PBS and blocked with 300 uL per well of 3% BSA in PBS for 2 hrs at room temperature. The wells were washed with PBS and were incubated with 50 nM biotin-labeled aptamers diluted in selection buffer for 2 hrs at room temperature. After washing, the bound aptamers were detected using streptavidin-horseradish peroxidase using standard procedures (FIG. 4).

Example 5: Binding of Selected Aptamers to Sepharose and Purifying Gelsolin

Selected aptamers were bound to Sepharose CL-2B beads was done using CNBr activation and coupling protocols described earlier (Arndt-Jovin et al, 1975; Kadonaga & Tjian, 1986). Briefly, the Sepharose beads were activated or derivatized using CNBr and then washed with ice-cold double-distilled water and 10 mM potassium phosphate (pH 8) and 5'-phosphorylated oligos were added to a thick slurry of the activated beads. The mixture was stirred at room temperature for 14 hours and washed with 1 M potassium phosphate (pH 8), 1 M KCl. Then the beads were washed with water, followed by 10 mM Tris-HCl (pH 8) containing 300 mM NaCl, 1 mM EDTA and 0.02% sodium azide. The functionalized beads were stored at 10° C. in the latter buffer.

For gelsolin purification experiments, the slurry of beads were poured in a PD-10 column and washed with three column volumes of 40 mM Tris buffer pH 8 containing 100 mM NaCl and 2 mM EGTA. To this column, cell lysate with pH adjusted to pH 8 and containing 2 mM EGTA was added. After initial loading, the column was washed with 40 mM Tris buffer pH 8 containing 100 mM of NaCl and 3 mM of $CaCl_2$ (three column volumes). Finally, elution was done by adding 40 mM Tris buffer pH 8 containing 300 mM NaCl and 20 mM $CaCl_2$. Each fraction was analyzed for the presence of gelsolin. Results (FIG. 5) support that gelsolin binds to DNA-immobilized column efficiently and elutes upon sensing higher levels of $Ca^{2+}$ ions. Final loading and elution conditions are still being worked upon to bind and purify much higher levels of gelsolin. After elution of gelsolin, the DNA-Sepharose was washed with 40 mM Sodium Acetate buffer pH 4 containing 300 mM NaCl. Column was regenerated by washing with 40 mM Tris buffer pH 8 containing 100 mM NaCl and 2 mM EGTA, and a second round of purification process was attempted. After washing the columns with 0.8 M NaCl, and washing the columns with 10× volume of 40 mM Tris buffer pH 8 containing 100 mM NaCl and 2 mM EGTA, five rounds of purification were done with little loss in efficiency in purifying tagless gelsolin.

Similar purification profiles were obtained upon functionalizing the claimed aptamers on other matrices as tested on Agarose, Superdex, Sephadex, Sephacryl, Sephacryl fast flow.

Example 6: Selected Aptamers Bind to Gelsolin and does not allow it to Bind Prion Causing Prp Protein Gelsolin binds to Prp protein and accelerates prion formation (unpublished work). Using structural data analysis and western blots we have confirmed that gelsolin directly binds to Prp. Later, we observed that the aptamers bind to gelsolin (FIG. 6) and does not allow it to bind Prp, thus blocking the gelsolin's role in prion disease progression. In these experiments, ELISA was performed to check whether binding of aptamer (10.10R) to gelsolin can inhibit the interaction of gelsolin with Prp. Monoclonal antibody against gelsolin was first coated in the wells to immobilize gelsolin (2 µg/well). After washings, Prp and Aptamer+Prp (mixture) were added. Also, in some wells, aptamer followed by PrP was added, so that the Aptamer and Prp in solution and can competitively inhibit their interaction with gelsolin. Bound Prp was detected using anti-Prp antibody (rabbit; 1:1000 dilutions), which was detected by anti-rabbit IgG antibody (1:3000). As mentioned earlier, absorbance values at 450 nm indicated the extent of bound Prp and results showed that aptamer 10.10R can inhibit the interaction of gelsolin and Prp.

Advantages of the Invention

Though the use of administration of recombinant gelsolin/its fragments has been reported earlier for therapeutic purposes in disease/health conditions accompanied by hypogelsolinemia, no reliable and mass producible gelsolin estimation or diagnostic method is available for therapeutic purposes. Additionally, an efficient protocol for mass production of gelsolin (particularly for constructs lacking any tags or groups for minimal step purification) remains a challenge.

- The developed DNA aptamers can replace the need for antibodies or actin—bringing in cost-effectiveness and better reproducibility in production and protocol steps without any loss of sensitivity and specificity.
- The use of immobilized aptamers on chromatographic material to purify gelsolin (or its variants), particularly after overproduction of gelsolin or its variants will have substantial advantage in purifying gelsolin lacking any affinity tags like his-tag, GST, MBP etc. Currently, minimal step purification of tagless-gelsolin is achieved by columns formed of immobilized anti-gelsolin antibodies. Another methodology involves ammonium sulphate based precipitation of gelsolin followed by its affinity binding on DEAE column, but this method requires 4-5 steps and suffers from significant loss of protein and time, during recovery from precipitated state.

REFERENCES

Arndt-Jovin D J, Jovin T M, Bahr W, Frischauf A M, Marquardt M (1975) Covalent attachment of DNA to agarose. Improved synthesis and use in affinity chromatography. *European journal of biochemistry/FEBS* 54: 411-418

Ashish, Paine M S, Perryman P B, Yang L, Yin H L, Krueger J K (2007) Global structure changes associated with Ca2+ activation of full-length human plasma gelsolin. *J Biol Chem* 282: 25884-25892

Bucki R, Byfield F J, Kulakowska A, McCormick M E, Drozdowski W, Namiot Z, Hartung T, Janmey P A (2008) Extracellular gelsolin binds lipoteichoic acid and modulates cellular response to proinflammatory bacterial wall components. *Journal of immunology* 181: 4936-4944

Bucki R, Georges P C, Espinassous Q, Funaki M, Pastore J J, Chaby R, Janmey P A (2005) Inactivation of endotoxin by human plasma gelsolin. *Biochemistry* 44: 9590-9597

Bucki R, Kulakowska A, Byfield F J, Zendzian-Piotrowska M, Baranowski M, Marzec M, Winer J P, Ciccarelli N J, Gorski J, Drozdowski W, Bittman R, Janmey P A (2010) Plasma gelsolin modulates cellular response to sphingosine 1-phosphate. *American journal of physiology Cell physiology* 299: C1516-1523

Garg R, Peddada N, Sagar A, Nihalani D, Ashish (2011) Visual insight into how low pH alone can induce actin-severing ability in gelsolin under calcium-free conditions. *J Biol Chem* 286: 20387-20397

Ito H, Kambe H, Kimura Y, Nakamura H, Hayashi E, Kishimoto T, Kishimoto S, Yamamoto H (1992) Depression of plasma gelsolin level during acute liver injury. *Gastroenterology* 102: 1686-1692

Kadonaga J T, Tjian R (1986) Affinity purification of sequence-specific DNA binding proteins. *Proceedings of the National Academy of Sciences of the United States of America* 83: 5889-5893

Kwiatkowski D J, Mehl R, Izumo S, Nadal-Ginard B, Yin H L (1988) Muscle is the major source of plasma gelsolin. *The Journal of biological chemistry* 263: 8239-8243

Kwiatkowski D J, Stossel T P, Orkin S H, Mole J E, Colten H R, Yin H L (1986) Plasma and cytoplasmic gelsolins are encoded by a single gene and contain a duplicated actin-binding domain. *Nature* 323: 455-458

Lee P S, Waxman A B, Cotich K L, Chung S W, Perrella M A, Stossel T P (2007) Plasma gelsolin is a marker and therapeutic agent in animal sepsis. *Crit Care Med* 35: 849-855

Lee W M, Galbraith R M (1992) The extracellular actin-scavenger system and actin toxicity. *N Engl J Med* 326: 1335-1341

Lind S E, Janmey P A (1984) Human plasma gelsolin binds to fibronectin. *J Biol Chem* 259: 13262-13266

Lind S E, Smith D B, Janmey P A, Stossel T P (1988) Depression of gelsolin levels and detection of gelsolin-actin complexes in plasma of patients with acute lung injury. *Am Rev Respir Dis* 138: 429-434

Lofberg M, Paunio T, Tahtela R, Kiuru S, Somer H (1998) Serum gelsolin and rhabdomyolysis. *J Neurol Sci* 157: 187-190

Osborn T M, Dahlgren C, Hartwig J H, Stossel T P (2007) Modifications of cellular responses to lysophosphatidic acid and platelet-activating factor by plasma gelsolin. *American journal of physiology Cell physiology* 292: C1323-1330

Osborn T M, Verdrengh M, Stossel T P, Tarkowski A, Bokarewa M (2008) Decreased levels of the gelsolin plasma isoform in patients with rheumatoid arthritis. *Arthritis research & therapy* 10: R117

Pan W, Clawson G A (2009) The shorter the better: reducing fixed primer regions of oligonucleotide libraries for aptamer selection. *Molecules* 14: 1353-1369

Peddada N, Sagar A, Ashish, Garg R (2012) Plasma gelsolin: a general prognostic marker of health. *Med Hypotheses* 78: 203-210

Peddada N, Sagar A, Rathore Y S, Choudhary V, Pattnaik U B, Khatri N, Garg R, Ashish (2013) Global shapes of F-actin depolymerization-competent minimal gelsolins: insight into the role of g2-g3 linker in pH/Ca2+ insensitivity of the first half. *J Biol Chem* 288: 28266-28282

Smith D B, Janmey P A, Sherwood J A, Howard R J, Lind S E (1988) Decreased plasma gelsolin levels in patients with Plasmodium falciparum malaria: a consequence of hemolysis? *Blood* 72: 214-218

Suhler E, Lin W, Yin H L, Lee W M (1997) Decreased plasma gelsolin concentrations in acute liver failure, myocardial infarction, septic shock, and myonecrosis. *Crit Care Med* 25: 594-598

Sun H Q, Yamamoto M, Mejillano M, Yin H L (1999) Gelsolin, a multifunctional actin regulatory protein. *The Journal of biological chemistry* 274: 33179-33182

Vouyiouklis D A, Brophy P J (1997) A novel gelsolin isoform expressed by oligodendrocytes in the central nervous system. *Journal of neurochemistry* 69: 995-1005

Wen D, Corina K, Chow E P, Miller S, Janmey P A, Pepinsky R B (1996) The plasma and cytoplasmic forms of human gelsolin differ in disulfide structure. *Biochemistry* 35: 9700-9709

Yin H L, Kwiatkowski D J, Mole J E, Cole F S (1984) Structure and biosynthesis of cytoplasmic and secreted variants of gelsolin. *J Biol Chem* 259: 5271-5276

Yin H L, Stull J T (1999) Proteins that regulate dynamic actin remodeling in response to membrane signaling mini-review series. *The Journal of biological chemistry* 274: 32529-32530

Yu F X, Zhou D M, Yin H L (1991) Chimeric and truncated gCap39 elucidate the requirements for actin filament severing and end capping by the gelsolin family of proteins. *J Biol Chem* 266: 19269-19275

---

We claim:

1. DNA aptamers represented by SEQ ID No. 6 capable of binding a protein gelsolin represented by SEQ ID No. 1 or its variants represented by SEQ ID No. 2 and 3.

2. A method for quantification of gelsolin levels in a sample using the DNA aptamers as claimed in claim 1, the method comprising:
   [a] coating 1 ug of streptavidin on a support using 100 mM NaHCO$_3$ buffer having pH 9.2 for 10 to 12 hours at a temperature of 4 degree C.;
   [b] washing the coated support obtained at step [a] with PBS and blocking with 3% BSA in the PBS for 2 hours followed by washing with the PBS;
   [c] labelling the aptamer with biotin;
   [d] immobilizing 2 uM of the biotin labeled aptamer on the support at step [c] using TE buffer having pH 8 supplemented with 2M NaCl for 2 hours at room temperature;
   [e] washing the support obtained at step [d] 2 times with the PBS containing 0.1% Tween-20;
   [f] adding the gelsolin in the range of 0.2 uM-5 nM or the sample diluted in selection buffer containing 0.1% BSA to the support obtained at step [e] and allowing to stand for 2 hours;
   [g] washing the support obtained in step 111 of step [f] 4 times with the PBS containing 0.1% Tween-20 followed by adding anti-gelsolin antibodies and incubating for 10 to 12 hours at 4 degree C.;
   [h] washing the support obtained in step [g] 4 times with the PBS containing 0.1% Tween-20 followed by adding secondary antibodies conjugated with horseradish peroxidase and incubating for 1 hour and then adding the substrate for the horseradish peroxidase; and
   [i] terminating the reaction of step [h] with 2M H$_2$SO$_4$ after the development of blue colour and measuring the absorbance at 450 nm so as to determine the quantity of gelsolin present in the sample.

3. A method for quantification of gelsolin in a sample using the DNA aptamers as claimed in claim 1, the method comprising:
   [a] coating anti-gelsolin antibodies on a support using 100 mM NaHCO$_3$ buffer having pH 9.2 for 10 to 12 hours at a temperature of 4 degree C.;
   [b] washing the coated support obtained at step [a] with PBS and blocking with 3% BSA in PBS for 2 hours followed by washing with the PBS;
   [c] adding the gelsolin in the range of 0.2 uM-5 nM or a sample diluted in the PBS containing 0.1% BSA and 0.01% Tween-20 to the support obtained at step [b] and allowing to stand for 2 hours at room temperature;
   [d] washing the support obtained at step [c] 3 times with PBS containing 0.1% Tween-20;
   [e] adding 1 uM of the biotin labeled aptamer diluted in selection buffer containing 0.1% BSA to the support obtained at step [d] and allowing to stand for 2 hours;
   [f] washing the support obtained at step [e] 4 times with the PBS containing 0.1% Tween-20 followed by adding streptavidin conjugated with horseradish peroxidase and incubating for 1 hour and then adding the substrate for the horseradish peroxidase; and
   [g] terminating the reaction of step [f] with 2M H$_2$SO$_4$ after the development of blue colour and measuring the absorbance at 450 nm so as to determine the quantity of gelsolin present in the sample.

4. A method for purification of gelsolin from a mixture using the DNA aptamers as claimed in claim 1, the method comprising:
   [a] activating Sepharose beads with CNBr;
   [b] washing the CNBr activated Sepharose beads with ice-cold double-distilled water and adding 10 mM potassium phosphate (pH 8) and 5'-phosphorylated oligo aptamers thereto to make a thick slurry of the activated beads;
   [c] stirring the slurry obtained at step [b] at room temperature for 14 hours and washing with 1 M potassium phosphate (pH 8) containing 1 M KCl;
   [d] washing the beads obtained at step [c] with water, followed by resuspending in 10 mM Tris-HCl (pH 8) containing 300 mM NaCl, 1 mM EDTA;
   [e] pouring the slurry of beads obtained at step [d] in a PD-10 column and washing with three column volumes of 40 mM Tris buffer pH 8 containing 100 mM NaCl and 2 mM EGTA;
   [f] adding to the column obtained at step [e], a cell lysate containing the gelsolin with pH adjusted to pH 8 and containing 2 mM EGTA;
   [g] washing the column of step [f] obtained after initial loading with three column volumes of 40 mM Tris buffer pH 8 containing 100 mM NaCl and 3 mM CaCl;
   [h] eluting the bound gelsolin from the column of step [g] by adding 40 mM Tris buffer pH 8 containing 300 mM of NaCl and 20 mM of CaCl$_2$.

* * * * *